(12) United States Patent
Fitch

(10) Patent No.: US 7,996,244 B1
(45) Date of Patent: Aug. 9, 2011

(54) SYSTEMS AND METHODS FOR MOBILE HEALTHCARE ALERTS

(75) Inventor: Todd M. Fitch, Santa Clara, CA (US)

(73) Assignee: Intuit Inc., Mountain View, CA (US)

( * ) Notice: Subject to any disclaimer, the term of this patent is extended or adjusted under 35 U.S.C. 154(b) by 918 days.

(21) Appl. No.: 11/742,249

(22) Filed: Apr. 30, 2007

(51) Int. Cl.
*G06F 19/00* (2011.01)
(52) U.S. Cl. .......................................................... 705/3
(58) Field of Classification Search .................. 705/2, 3, 705/4, 75; 368/10
See application file for complete search history.

(56) References Cited

U.S. PATENT DOCUMENTS

| | | | | |
|---|---|---|---|---|
| 5,337,290 | A | * | 8/1994 | Ventimiglia et al. ............ 368/10 |
| 7,698,230 | B1 | * | 4/2010 | Brown et al. .................... 705/75 |
| 2003/0097280 | A1 | * | 5/2003 | Fitzpatrick et al. ............... 705/2 |
| 2004/0103000 | A1 | * | 5/2004 | Owurowa et al. ................. 705/2 |
| 2004/0186746 | A1 | * | 9/2004 | Angst et al. ....................... 705/3 |
| 2006/0085347 | A1 | | 4/2006 | Yiachos |
| 2008/0027752 | A1 | * | 1/2008 | Phan et al. ........................ 705/2 |

OTHER PUBLICATIONS

"MedicAlert—E-HealthKEY", http://web.archive.org/web/20070419205114/http://www.medicalert.org/E-Health/, web archive dated Apr. 19, 2007 (medicalert_E-Health).
"MedicAlert—Emblems", http://web.archive.org/web/20070324040635/http://www.medicalert.org/Home/HomeEmblemCatalogs.aspx, web archive dated Mar. 24, 2007 (medicalert_emblem).

* cited by examiner

*Primary Examiner* — Gerald J. O'Connor
*Assistant Examiner* — John A Pauls
(74) *Attorney, Agent, or Firm* — Gunnison, McKay & Hodgson, L.L.P.; Philip McKay

(57) ABSTRACT

Various embodiments of a method and apparatus for a portable medical alert mechanism stores health information on a portable electronic device and provides the health information to a health professional. In some embodiments, the health information may include information about a health condition, a health history, current medications, current medication dosages, allergies, or instructions. The health information may be on the portable electronic device and/or downloaded from a web-based application. In some embodiments, the health information may be selected and transferred to the portable electronic device by the system user from an external computer system. The health information stored on the portable electronic device may be periodically updated. The system user (or the portable electronic device) may have an indication of the presence of the health information on the portable electronic device (e.g., on a bracelet).

13 Claims, 12 Drawing Sheets

Portable Electronic Device Download
301

John Doe — 319
1234 Address Lane
Anycity, Anystate 99999

Primary Health Conditions: — 321
High Blood Pressure
Diabetic

PIN: 5684 — 323

Please check boxes corresponding to
information you wish to download:

☐ Entire Health History (10.5 MB) — 303, 305
☒ Recent Health History (1 year) (3.2 MB) — 307
☒ Emergency Responder Information (534 Kb) — 309
☒ Health History Access Link and Instructions (58 Kb)

Emergency Responder Information: — 325

☒ Current Medications — 311
☒ Allergies — 313
☐ Emergency Instructions — 315
☒ Emergency Contact Information — 317

Emergency Information:

John Doe
1234 Address Lane — 501
Anycity, Anystate 99999

Current Health Conditions: High Blood Pressure and Diabeties — 503

Current Medications: Chlorthalidone, acebutolol, and tolbutamide — 505

Emergency URL: http://999.99.999.999/emergency_info — 507

Allergies: No Known Allergies — 509

Emergency Contact Information:

Emergency Contact: Jane Doe (Wife)
Phone Number: (999) 993-9999 — 511

Recent Health History (1 year) Available — 513

*FIG. 5*

Add Current Prescriptions? — 911

We currently show you have prescriptions to:

Medication #1

Medication #2

Do you want to list your prescriptions in your portable health information?

< Back          Yes     No

901

Final
Changes
Instructions — Emergency Medications
Allergies — 903
Dosages
Medications — 905
Current Prescriptions
Health Conditions — 907

FIG. 9

Download Portable Health History to mobile phone #1 ((999) 999-9999)?

Portable Health History to Download:
- health condition
- prescriptions and dosages
- allergies
- emergency contact information
- Recent Health History
- Health History Access Link and Instructions

1101

Do you want to download to mobile phone #1?

< Back     Yes     No

Tabs: Health Conditions | Final Review | Medications | Download | Allergies | Instructions | Confirm Download | Changes | Final

FIG. 11

SYSTEMS AND METHODS FOR MOBILE HEALTHCARE ALERTS

BACKGROUND

People who have medical problems (especially medical problems which may result in an emergency situation) may wear a bracelet or necklace with the name of the condition they have to let emergency responders know what problem may be causing the emergency. However, only providing the condition may not provide health professionals with necessary information they need to treat the person. This may result, for example, in emergency responders giving medication or treatment which may interfere with medication the patient is currently taking or, medication the patient is allergic to.

People often carry with them portable electronic devices such as portable mobile phones, personal digital assistants (PDA), electronic watch, portable audio players, and portable game players. These devices may be capable of storing a large amount of information and may be on or near their owner when their owner is having an emergency.

SUMMARY

Various embodiments of a method and apparatus for a portable medical alert mechanism may store health information on a system user's portable electronic device (e.g., a mobile phone, a personal digital assistant (PDA), electronic watch, portable audio player, or a portable game player) and provide the health information to a health professional (e.g., an emergency medical technician, a physician, physician's assistant, a nurse, etc.). In some embodiments, the health information may include information about a health condition, a health history, current medications, current medication dosages, allergies, instructions, etc. for the system user. In some embodiments, the health information may include a link (e.g., a uniform resource locator (URL)) to health information (which may be additional health information). In some embodiments, a security identifier may be required prior to providing the health information to the health professional.

In some embodiments, the portable electronic device may be operable to alert the health professional to the presence of the health information. For example, the portable electronic device may include a sticker or casing alerting a health professional as to the presence of the information. In some embodiments, the system user of the portable device may wear an indication of the presence of the health information on the portable electronic device. For example, the indication may include a bracelet with information pointing to the health information on the portable electronic device.

In some embodiments, the health information may be transferred to the portable electronic device from another computer system. The health information provided to the portable electronic device may be at least partially selected by the system user of the portable electronic device. In some embodiments, the system user may select the health information through a system user interface provided by the computer system. In some embodiments, the health information may be downloaded from a web-based healthcare management application. In some embodiments, the health information stored on the portable electronic device may be updated (e.g., periodically).

BRIEF DESCRIPTION OF THE DRAWINGS

FIG. 3 illustrates a system user interface to assist a system user in selecting the information the system user wants to download to the system user's portable electronic device, according to an embodiment.

FIG. 5 illustrates a display of the portable electronic device displaying health information for the system user, according to an embodiment.

FIG. 9 illustrates a user interface for determining which information to include in the portable health information, according to an embodiment.

FIG. 11 illustrates a user interface for downloading the portable health information, according to an embodiment.

While the invention is described herein by way of example for several embodiments and illustrative drawings, those skilled in the art will recognize that the invention is not limited to the embodiments or drawings described. It should be understood, that the drawings and detailed description thereto are not intended to limit the invention to the particular form disclosed, but on the contrary, the intention is to cover all modifications, equivalents and alternatives falling within the spirit and scope of the present invention as defined by the appended claims. The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including, but not limited to.

DETAILED DESCRIPTION OF EMBODIMENTS

Figure 1:
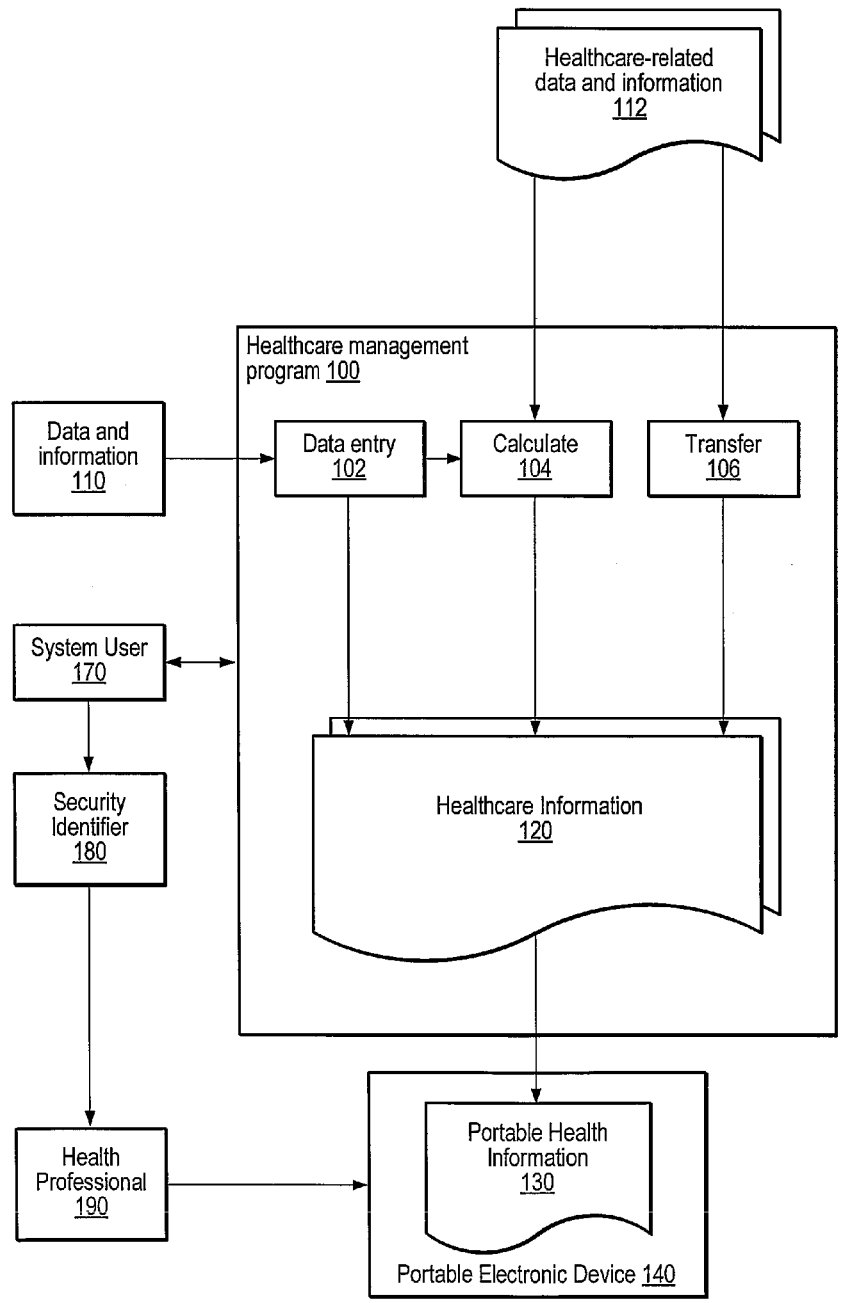
FIG. 1 illustrates the preparation of healthcare information using a healthcare management application, according to an embodiment.
Figure 2:
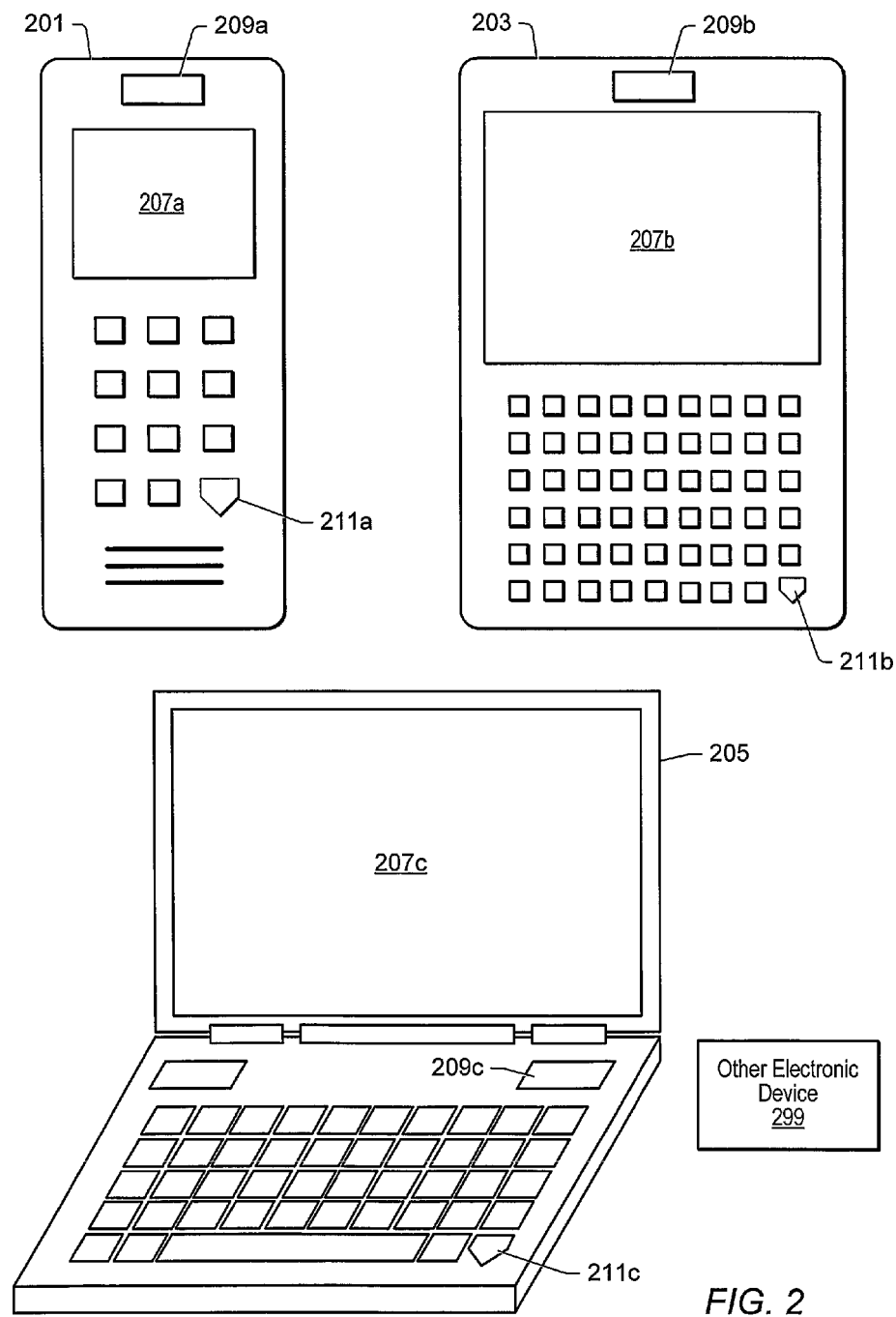
FIG. 2 illustrates several portable electronic devices, according to an embodiment.

Various embodiments of a method and apparatus for a portable medical alert mechanism may store portable health information 130 for a system user 170 on a portable electronic device 140 carried with the system user 170 and may provide the portable health information 130 to a health professional 190 (e.g., during an emergency involving the system user 170). As seen in FIG. 1, the portable health information 130 may be from healthcare information 120 stored using a healthcare management application 100 (discussed further below). As seen in FIG. 2, portable electronic devices 140 may include a mobile phone 201, a personal digital assistant (PDA) 203, a laptop 205, or other electronic device 299 (e.g., a portable audio player, electronic watch, or a portable game player). Other portable electronic devices 140 are also contemplated. Health professionals 190 may include emergency medical technicians, physicians, physician's assistants, nurses, etc. As used herein, a "health professional 190" may be any entity interested in the health of the system user 170 and is not limited to health professionals 190 who diagnosis and/or treat health problems. The portable health information 130 may be stored on a memory 1297 (see FIG. 12) on the portable electronic device 140 and/or may be accessible to the portable electronic device 140 through a network (e.g., stored on a remote computer and accessed through the Internet). Other storage mechanisms are also possible. The portable health information 130 may be provided, for example, by displaying the portable health information 130 on a display 207 (e.g., a word file may be displayed on mobile phone display 207a, PDA display 207b, or laptop display 207c) and/or through a speaker 209 (e.g., an audio file may be played on mobile phone speaker 209a, PDA speaker 209b, or laptop speaker 209c) of the portable electronic device 140. Other file formats are also possible (e.g., a video file). In some embodiments, the portable health information 130 may be provided to health professionals 190 by being transmitted (e.g., wirelessly) to a health professional 190's portable electronic device.

In some embodiments, the stored/provided portable health information 130 may include information about a system user's health condition, personal health history, personal health record, current medications, current medication dosages, allergies (e.g., allergies to bee stings, peanuts, penicillin, etc.), and/or emergency instructions to health professionals 190. Other information is also contemplated. The portable health information 130 stored on the portable electronic device 140 and provided to health professionals 190 may be useful to the health professionals 190, for example, during a medical emergency involving the system user 170. For example, if the system user 170 is a diabetic and loses consciousness during insulin shock, responding medical technicians may receive portable health information 130 from the system user's portable electronic device, including the system user's health condition, and may be able to quickly treat the system user 170 accordingly. In some embodiments, the system user 170 may at least partially select what portable health information 130 (e.g., from the health information 120) to include on the portable electronic device 140 (e.g., using the interface shown in FIG. 3). The portable health information 130 stored on the portable electronic device 140 may be used to determine the health condition causing the medical emergency and/or what medications are currently prescribed to the system user 170. Information about allergies may also indicate to the health professionals 190 which medications to avoid giving the system user 170. In some embodiments, the portable health information 130 may include instructions to the health professionals 190 (e.g., the identity of a specific medication to give the system user 170 or a course of treatment to administer during an emergency). The portable health information 130 may also include the name of a doctor and/or facility to contact in case of an emergency. In some embodiments, the portable health information 130 on the portable electronic device 140 may be used by health professionals 190 during a non-emergency event (e.g., a doctor visit).

Figure 4:
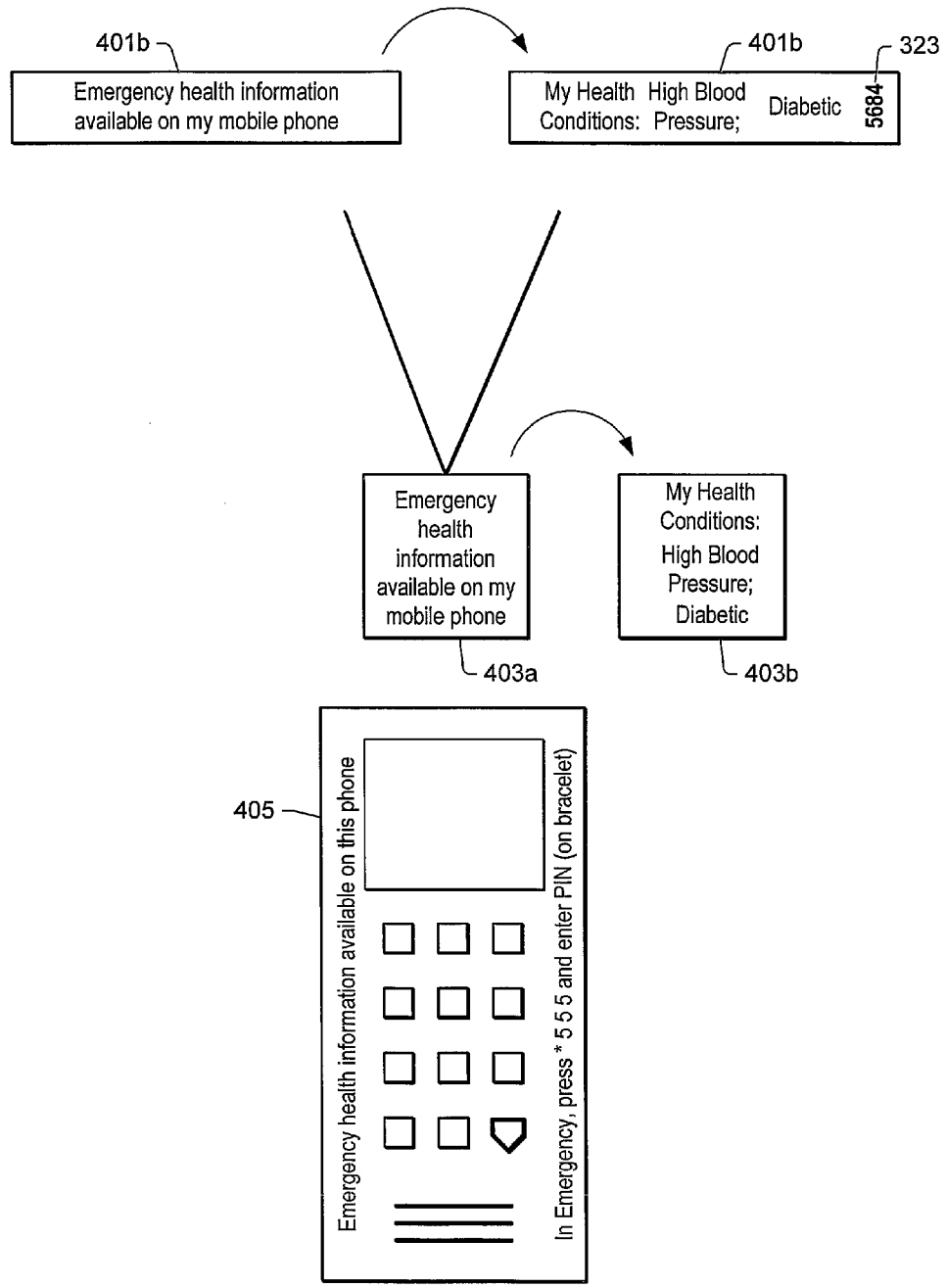
FIG. 4 illustrates embodiments of a bracelet, necklace and phone casing, according to an embodiment.

In some embodiments, the portable electronic device 140 may be operable to alert the health professionals 190 to the presence of the portable health information 130. For example, as seen in FIG. 4, the portable electronic device 140 may include a sticker or skin 405 (e.g., a plastic mobile phone casing) alerting the health professional 190 as to the presence of the portable health information 130. In one embodiment, a label reading "Emergency health information available on this device" (or similar type label) may be placed on the outside of the portable electronic device 140. In some embodiments, the indication may include a recognizable icon (e.g., recognizable to responding health professionals 190). For example, the recognizable icon may be placed on the outside of the portable electronic device 140 and/or presented on the electronic interface of the portable electronic device 140. In some embodiments, the system user 170 of the portable electronic device 140 may wear an indication of the presence of the portable health information 130 on the portable electronic device 140. For example, the indication may include a bracelet 401 (see front 401a, back 401b) or necklace 403 (see front 403a, back 403b) worn by the system user 170 with information relative to the portable health information 130 on the portable electronic device 140 (e.g., the bracelet 401 may indicate the system user's health condition and/or have a similar label (see above) pointing to the information on the portable electronic device 140). In some embodiments, the indication (e.g., the bracelet 401 or necklace 403) may include instructions on how to access the portable health information 130. In some embodiments, a button 211 (e.g., button 211a, 211b, or 211c) on the portable electronic device 140 may be marked with the recognizable icon. Pressing the button 211 may activate an interface for viewing the portable health information 130. In some embodiments, pressing and holding a button on the portable electronic device (e.g., pressing and holding the "8" key) may activate the interface for viewing the portable health information 130.

In some embodiments, (e.g., upon seeing the indication of the portable health information 130) the health professional 190 may activate the portable electronic device 140 to access the portable health information 130 (e.g., which may be presented as shown in FIG. 5). In some embodiments, the portable electronic device 140 may require a security identifier 180 (e.g., a Personal Identification Number (PIN)) prior to providing the portable health information 130. The system user 170 may provide the security identifier 180 to the health professional 190 or the system user 170 may access the portable health information 130 and hand the portable electronic device 140 to the health professional 190 for their review. In some embodiments, the security identifier 180 may be placed on the bracelet 401. In some embodiments, the security identifier 180 may include a fingerprint or retina scan (provided by the system user 170). In some embodiments, several tiers of information may be made available based on the provided security identifier 180. For example, a high level tier of information (including the system user's health condition and allergies) may be provided if at least the PIN is provided. Additional information such as the system user's current medications (a second tier) may be provided if a fingerprint scan can be provided. This may allow for some additional security while at the same time allowing health professionals 190 to at least see a first tier of information in case the system user 170 is unable to provide a security identifier 180 for the second tier. In some embodiments, no security identifier 180 may be required to see the portable health information 130. This may be useful where the system user 170 has a critical condition (e.g., severe heart disease) that requires full disclosure of portable health information 130 to health professionals 190 even if the system user 170 is unable to provide a security identifier 180.

Figure 6:
FIG. 6 illustrates a display of the web-based health information for the system user, according to an embodiment.

In some embodiments, the portable health information 130 may include a link (e.g., a URL) to web-based information (e.g., see FIG. 6). In some embodiments, the personal electronic device 140 may access the Internet directly for the web-based information and/or the health professional 190 (or system user 170) may access the Internet through another device (e.g., a laptop 205 with wireless connectivity) to access the web-based information. In some embodiments, the web-based information may be stored on and accessed from a storage device that is not necessarily coupled to the Internet (e.g., a storage device on a system user's home computer or a storage device worn by the system user 170). In some embodiments, a second security identifier 180 (e.g., a username and/or password) may be required to access the web-based information. In some embodiments, the same security identifier 180 as used to access the portable health information 130 on the portable electronic device 140 may be used to access the web-based information. The web-based information may include, for example, the system user's health history. Other information may also be accessible (e.g., blood test results, X-rays, recent electrocardiograms (EKG), other test results, etc.). The web-based health information may also include psychological information, dental records, vision information (e.g., contact lens size and/or prescription), etc. In some embodiments, this information may also be stored on the portable electronic device 140.

In some embodiments, as noted above, the system user 170 may at least partially select what health information 120 to download to the portable electronic device 140 (e.g., from the healthcare management application 100 or another collection of health information maintained for the system user 170 on a network based health information system). The selected portable health information 130 to be stored on the portable electronic device 140 may be entered directly into the portable electronic device 140 by the system user 170 or the information may be transmitted to the portable electronic device 140 from an external computer (e.g., a remote computer on the Internet). In some embodiments, the system user 170 may select the portable health information 130 through a system user interface 301 provided by the computer system. In some embodiments, the portable health information 130 may be downloaded from a healthcare management application 100 accessible through the computer system (e.g., the healthcare management application 100 may be web-based). In some embodiments, the portable health information 130 stored on the portable electronic device 140 may be updated (e.g., by the system user 170 or by the healthcare management application 100). In some embodiments, the portable health information 130 may be periodically updated on the portable electronic device 140.

In various embodiments, the healthcare management application 100 may provide the system user 170 with a framework and tools for collecting, organizing, and managing data and information (e.g., data and information 110 and healthcare-related data and information 112) related to their health history; past, current and future health services; health insurance plan(s) (e.g., what services are covered, coverage limits, claims status, and explanations of benefits); and finances related to healthcare (e.g., health insurance premiums, deductibles, co-payments, benefit payments, reimbursements from Flexible Spending Accounts (FSAs), Health Reimbursement Accounts (HRAs), or health savings accounts, maximum out-of-pocket expenses, and maximum lifetime benefits.) For example, a healthcare management application 100 may be configured to provide a system user 170 with a comprehensive and detailed health history, or may allow the system user 170 to extract and/or analyze his or her data regarding a particular health condition or event (e.g., an injury or illness) or a particular healthcare-related service (e.g., a particular diagnostic exam or a course of treatment for a chronic condition.) In some embodiments, the healthcare management application 100 may also provide heuristic algorithms to assist the system user 170 in determining what health information 120 to download to their portable electronic device 140. In some embodiments, the heuristic algorithms may automatically determine what health information 120 to download to the portable electronic device 140 without system user intervention.

The healthcare management application 100 may in some embodiments be implemented as a web-based service to which system users 170 and/or employers may subscribe. In other embodiments, it may be implemented as a stand-alone application, such as one installed and executed on a desktop computer by a system user 170. In some embodiments, the healthcare management application 100 may include both a locally installed application (i.e., a client portion) and a remote, web-based application (i.e., a server portion). For example, in one embodiment, the system user 170 may enter healthcare-related information on a locally installed client application and then may upload the information to a healthcare management service server for secure storage and/or further analysis.

In various embodiments, the healthcare management application 100 may receive information (e.g., through data entry 102 and/or transfer 106) from one or more of: a system user 170, one or more healthcare providers, one or more health plan administrators (e.g., health insurance representatives), and one or more financial institutions. In some embodiments, the information received and/or managed by a healthcare management application 100 may be formatted according to a standard data exchange format.

A healthcare management application 100 may in some embodiments maintain healthcare-related information in one or more databases (or in other suitable formats) in a local or remote memory, or in a combination of the two. For example, a database located on a healthcare management service server may be configured to securely store healthcare-related information for multiple individual system users 170 or for employees of one or more corporations subscribing to the healthcare management service, while a database stored locally on a system user's computing system may include only his or her own personal healthcare-related data.

FIG. 1 illustrates the preparation of healthcare information 120 using a healthcare management application 100 according to one embodiment. Healthcare management application 100 may be configured to guide the system user 170 through the healthcare management application 100 step-by-step, and may automatically perform necessary healthcare management in accordance with data input, forms, tables, and formulas stored with or coded into the program.

Figure 12:
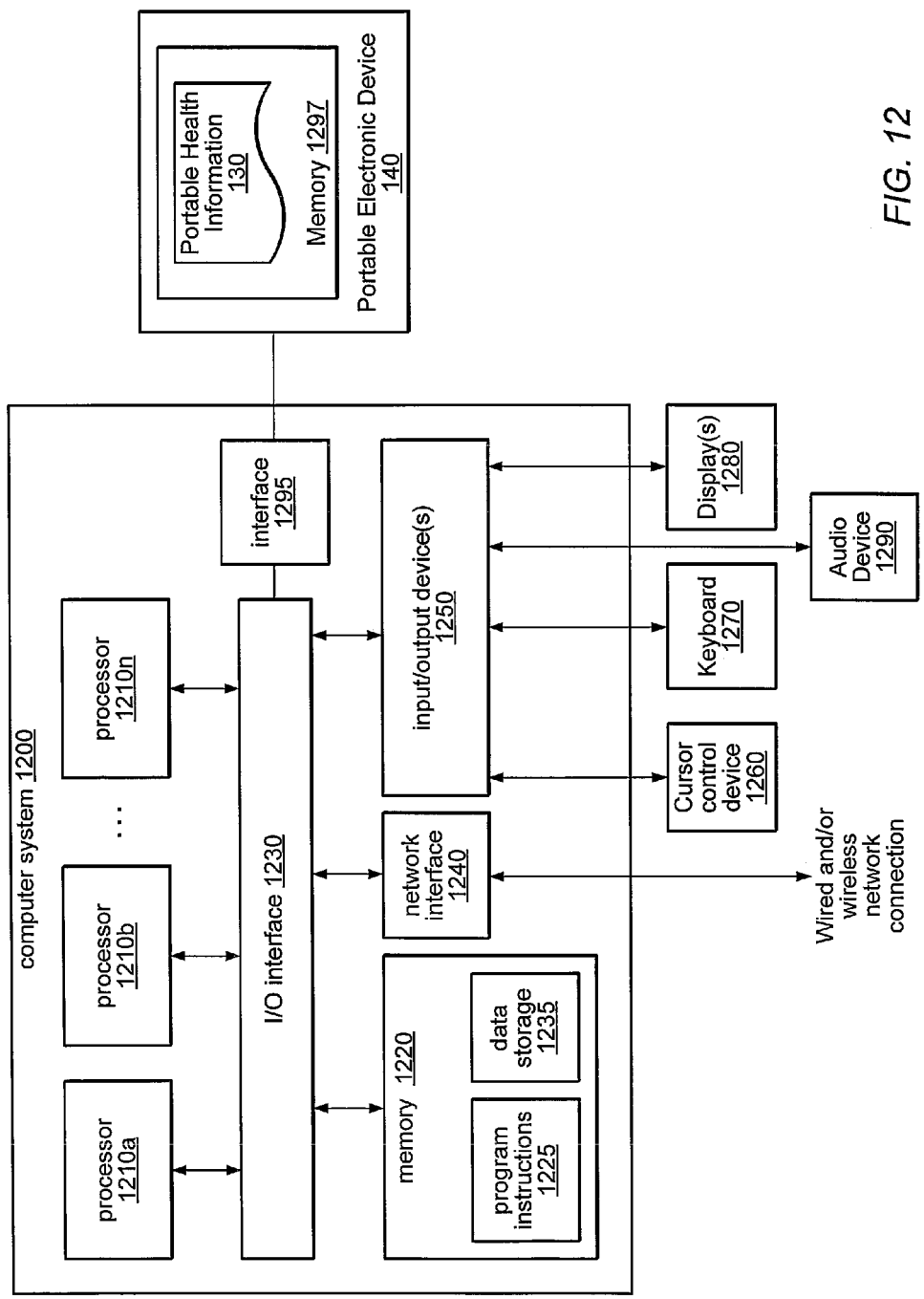
FIG. 12 illustrates a computer system, according to an embodiment.

An instance of healthcare management application 100 may be installed and executed on a computer system. The computer system may be a personal computer (PC) such as a desktop computer, laptop computer 205, mobile phone 201, TV set-top boxes, PDA 203, or other computing device. An exemplary computer system on which an instance of healthcare management application 100 may be implemented is illustrated in FIG. 12. In some embodiments, the healthcare management application 100 may be a network- or web-based healthcare information application which a system user 170 may access (e.g., via a web browser or other application on the system user's local computer system) to prepare various healthcare information forms via a network connection to a remote computer system (e.g., a server), without necessarily installing a healthcare management application 100 on the local computer system.

In some embodiments, the system user 170 may access or execute healthcare management application 100 to manage healthcare information for the system user 170. Note that the healthcare facility may be a person (e.g., a doctor), a business (e.g., a hospital), or other entity for which healthcare information 120 is to be prepared and/or stored. Further, the healthcare information 120 may be maintained for two or more system users 170 (e.g., a family). The healthcare information 120 may be current healthcare information being accessed for monitoring healthcare billing, insurance payments/deductibles, etc.

Healthcare management application 100 may provide a system user interface to guide or step the system user 170 in the preparation and storage of healthcare information 120. Different areas for preparing healthcare information 120 for different healthcare facilities may be identified as different modules in the healthcare management application 100. Healthcare information 120 may be associated with a particular module (e.g., recently received medical bills, insurance payouts, insurance premiums, etc.) in the healthcare management application 100. Thus, healthcare management application 100 may provide a system user interface that allows the system user 170 to select an appropriate module from among two or more modules for preparing healthcare information 120 for filing with a particular healthcare facility.

The healthcare management application 100 may include healthcare documents—e.g., forms, bills, insurance reports, etc. included in the stored healthcare information 120. In some implementations, these healthcare documents may be graphically presented by the healthcare management application 100 to the system user 170 on a display device (e.g., a computer monitor or screen of a hand-held device such as a PDA 203). In some embodiments, the healthcare management application 100 will provide a data entry mechanism 102 via a system user interface with various system user interface elements (menus, dialog boxes, etc.) and system user-selectable interface items (menu items, buttons, controls, text entry boxes, etc.) whereby the system user 170 may access the documents as needed and enter or modify data on the various healthcare documents using one or more data entry/cursor control mechanisms, such as a keyboard and mouse. These documents may be presented on the system user interface as templates that, when partially or completely filled out, may be "saved" for the particular healthcare facility for which the documents are prepared.

In addition, information from previous and/or related healthcare information and/or from other sources or documents may be transferred 106 into or used in the calculation 104 of values for fields of the electronic healthcare documents. Further, values from a field or fields on one or more electronic healthcare documents may be transferred 106 to other electronic healthcare documents. For example, a calculated value from a bill may be transferred into or used in the calculation of a field (e.g., a required payment) on another electronic healthcare document.

Instead of or as an alternative to entering the necessary data and information directly to the electronic healthcare documents, some implementations of the healthcare management application 100 may provide an input mechanism whereby the system user 170 inputs necessary data and information into input fields on data entry displays presented to the system user 170 by healthcare management application 100 as electronic healthcare documents. Note that data and/or information from other sources, which may include data and/or information from a previous healthcare information 120, from other data entry displays, or from other electronic healthcare documents related to the preparation of the healthcare information 120 under preparation, may be transferred into or used in the calculation of values for some fields in the data entry displays. Data and information from the data entry displays may then be automatically transferred into the appropriate locations on electronic healthcare information documents and/or onto other data entry displays. The healthcare management application 100 may perform any necessary calculations using the data and information from the data entry displays, and possibly data and information from other sources such as previous healthcare information 120 to generate appropriate calculated values for certain fields of the healthcare information documents.

In addition to system user entered or transferred values, the healthcare management application 100 may perform various calculations 104 to generate values for some fields in electronic healthcare documents. Note that inputs to a particular calculation to generate a value for a field may include one or more values from one or more sources. One or more data values entered by the system user 170 via the data entry system user interface may be used in calculations to generate new values from some fields in electronic healthcare documents. In some cases, one or more values from previous healthcare information 120 may be used in calculations to generate new values for some fields. Calculated values or values from fields on electronic healthcare documents may be used as input into other calculations. Also note that some values used in calculations may be coded as "constants" into the healthcare management application 100, or alternatively may be read into the healthcare management application 100 from a stored data file as needed.

In some embodiments, the system user 170 will enter necessary data and information via the system user interface of the healthcare management application 100, and, when done, access the system user interface to direct the healthcare management application 100 to complete the healthcare information 120 under preparation. The healthcare management application 100 may perform any necessary calculations using the entered data and information and in accordance with healthcare information formulas relevant to the particular healthcare information 120 under preparation, and possibly data and information from other sources such as previous healthcare information or other healthcare-related documents, to generate appropriate calculated values for certain fields of the healthcare information 120 under preparation.

Note that instances of healthcare management application 100 may be installed and executed on many computer systems and used by many system users 170 to prepare various healthcare documents and manage healthcare information. Alternatively, healthcare management application 100 may be a network- or web-based healthcare information preparation program which many system users 170 may access (e.g., via web browsers or other applications on the system users 170' local computer systems) to prepare various healthcare information forms via network connections to one or more remote computer systems (e.g., servers), without necessarily installing a healthcare management application 100 on the local computer systems.

Figure 7:
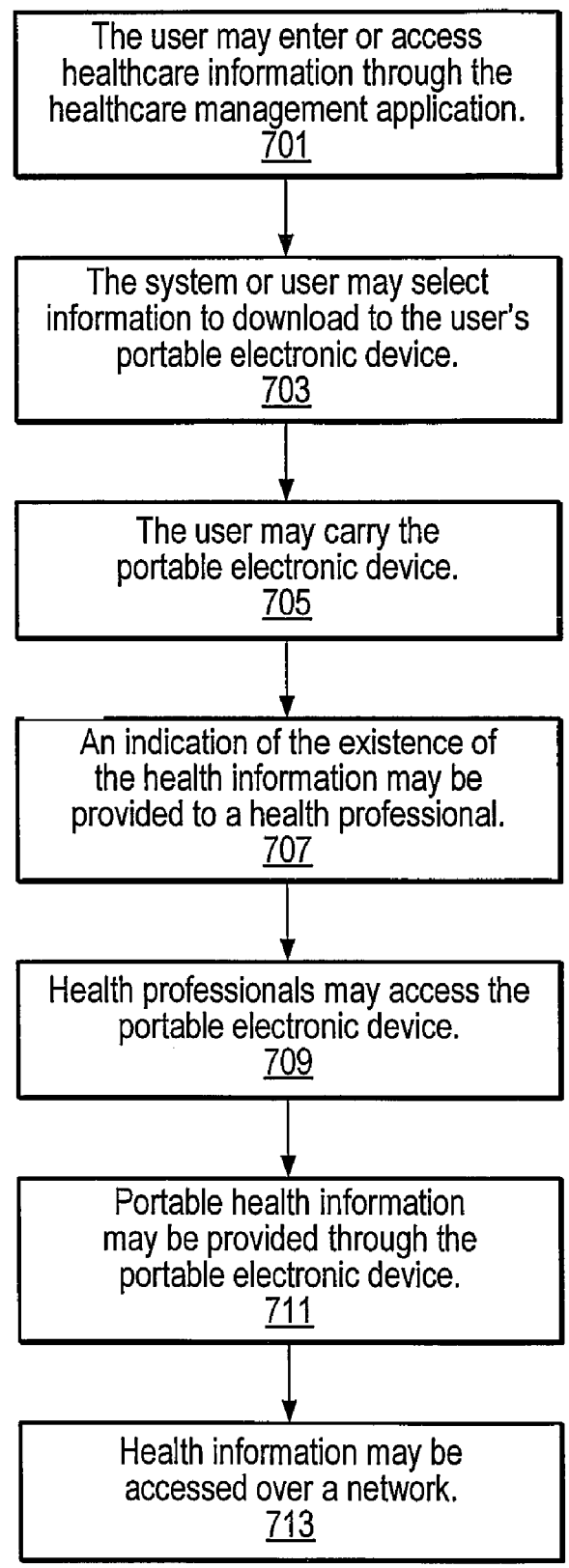
FIG. 7 illustrates a flowchart of a method for using the mobile healthcare alert system to provide health professional with health information, according to an embodiment.

FIG. 7 illustrates a flowchart of a method for using the mobile healthcare alert system to provide health professionals 190 with portable health information 130, according to an embodiment. It should be noted that in various embodiments of the methods described below, one or more of the elements described may be performed concurrently, in a different order than shown, or may be omitted entirely. Other additional elements may also be performed as desired.

At 701, the system user 170 may enter or access healthcare information 120 through the healthcare management application 100. The system user 170 may use the healthcare management application 100 to collect, organize, and manage data related to their health history; past, current and future health services; health insurance plan(s); and finances related to healthcare. For example, the system user 170 may maintain and update their personal health history and/or personal health record through the healthcare management application 100. This information may also be used to provide the portable health information 130 for the system user's portable electronic device.

At 703, the system or system user 170 may select information (e.g., from the healthcare management application 100) to download to the system user's portable electronic device 140. As seen in FIG. 3, the system user 170 may use the system user interface 301 to indicate what information the system user 170 wants to download to the system user's portable electronic device 140. For example, the system user 170 may indicate with one or more check boxes which options the system user 170 wants to download. In the example shown, the system user 170 has selected "Recent Health History" 305, "Emergency Responder Information" 307, and "Health History Access Link" 309 and not selected "Entire Health History" 303. Additional options may be selected or additional information may be provided through other panels as well. For example, additional information may be indicated/provided in the "Emergency Responder Information" panel 325. In the example shown, the system user 170 has selected "Current Medications" 311, "Allergies" 313, and "Emergency Contact Information" 317 as information to include in the download (and not selected Emergency Instructions 315). Text boxes (e.g., text box 327) may also be used by the system user 170 to provide additional information. In some embodiments, other information may be included with the information downloaded. For example, the system user's name and address 319, primary health conditions 321, and PIN 323 may be shown. In some embodiments, the PIN 323 may be selected and changed by the system user 170. Other information and selection formats are also contemplated. In some embodiments, individual files with health information 120 may be selected for download. In some embodiments, an interactive system user interface (e.g., a series of panels) may provide a heuristic approach to selecting which information to download to the portable electronic device 140 (e.g., see FIG. 8). In some embodiments, information may be downloaded through a short message system (SMS) format (other formats are also contemplated).

At 705, the system user 170 may carry the portable electronic device 140 with them (e.g., during normal daily activities). For example, the portable electronic device 140 may be a mobile phone 201 the system user 170 uses to make phone calls during the day. The portable electronic device 140 may also be the system user's PDA 203 or laptop 205. In some embodiments, the system user 170 may carry multiple portable electronic devices 140 (one or more of which may include the portable health information 130). Because the portable electronic device 140 is portable (and may be frequently used by the system user 170) there is an increased chance that the portable electronic device 140 will be with the system user 170 in the event of an emergency and/or when the system user 170 needs the portable health information 130.

At 707, an indication of the existence of the health information may be provided to a health professional. As seen in FIG. 4, the system user 170 may be wearing a bracelet 401 (front 401*a*, back 401*b*) (other arrangements are also possible) with the indication. In some embodiments, the system user 170 may be wearing a necklace 403 (front 403*a*, back 403*b*) (other arrangements are also possible). Other items may also be worn on or near the system user 170 (e.g., a card in the system user's wallet). In some embodiments, an indication may be placed directly on the portable electronic device 140 (e.g., outer casing 405 for a mobile phone 201). Messages placed on the bracelet 401, necklace 403, outer casing 405, or other items may include an indication of the availability of the information on the portable electronic device 140 (e.g., "Emergency Health Information Available on My Mobile Phone"). The messages on the bracelet 401, necklace 403, outer casing 405 or other items may include information about the system user's health conditions, instructions on how to access the information on the portable electronic device 140, and/or a security identifier 180 such as PIN 323. The messages may include, for example, "My Health Conditions: High Blood Pressure; Diabetic" or "In Emergency, press * 5 5 5 and enter PIN (on bracelet)." Other messages are also contemplated. In some embodiments, an icon (e.g., recognizable by health professionals 190) may be placed on or near the system user 170 (e.g., on the portable electronic device 140) that may indicate to the health professionals 190 the existence of the portable health information 130 on the portable electronic device 140.

At 709, health professionals 190 may access the portable electronic device 140. For example, if the system user 170 experiences an emergency, a health professional 190 (such as a firefighter or paramedic) may see the system user's bracelet 401 or necklace 403 and know to access the system user's portable electronic device 140 for information about the system user's health condition. The health professional 190 may also read the instructions as to how to access the information on the portable electronic device 140. In some embodiments, the portable health information 130 may be made available through instructions provided by the portable electronic device 140. For example, when active, the portable electronic device 140 may have a message "In emergency, press" in front of a button that can be pressed to access and/or display the system user's portable health information 130. Other methods of accessing the portable health information 130 are also contemplated. For example, the system user 170 may access the portable health information 130 on the portable electronic device 140 and may relay the information to the health professionals 190 or may hand the portable electronic device 140 to the health professionals 190. In some embodiments, after entering a security identifier 180, the portable electronic device 140 may transmit the portable health information 130 to a portable electronic device of the health professionals 190. In some embodiments, the portable electronic device 140 may project at least a portion of the portable health information 130 and/or sound out at least a portion of the portable health information 130 (e.g., through a speaker on the portable electronic device 140).

At 711, portable health information 130 may be provided through the portable electronic device 140. FIG. 5 illustrates an embodiment of a display of the portable electronic device 140 displaying portable health information 130 for the system user 170. In some embodiments, portable health information 130 provided to the health professional 190 may include name and address 501, current health conditions 503, current medications 505, allergies 509, emergency contact information 511 and other information. In some embodiments, a URL 507 may be provided to the health professional 190 to use to access additional information about the system user's health conditions. In the embodiment shown in FIG. 5, the system user 170 made available their recent health history 513 (accessible by scrolling down as indicated by the down arrow). Other ways of accessing the recent health history (or other documents made available) are also contemplated (e.g., clicking an icon, voice access, etc.).

At 713, health information (e.g., additional health information) may also be accessed over a network. In some embodiments, the health information accessible over the network may be a subset of the total health information available for the system user 170. In some embodiments, the health professionals 190 may use the provided URL 607 to access additional information. In some embodiments, the additional information may be accessed by a doctor at a hospital. Once the URL 607 is entered (e.g., into the portable electronic device 140 or an external computer system), a system username and password may be required (these may be provided by the system user 170). In some embodiments, the information may be accessed over the network in another way. In some embodiments, a system username and password may not be required. In some embodiments, the information shown may include the name 601, health conditions 603, medications and dosages 605, allergies 607, and contact information 611. The information may include a full health history file 613 that may be viewed directly or provided as a download. Other information may also be made available. In some embodiments, other combinations of information may be made available over the network.

Figure 8:
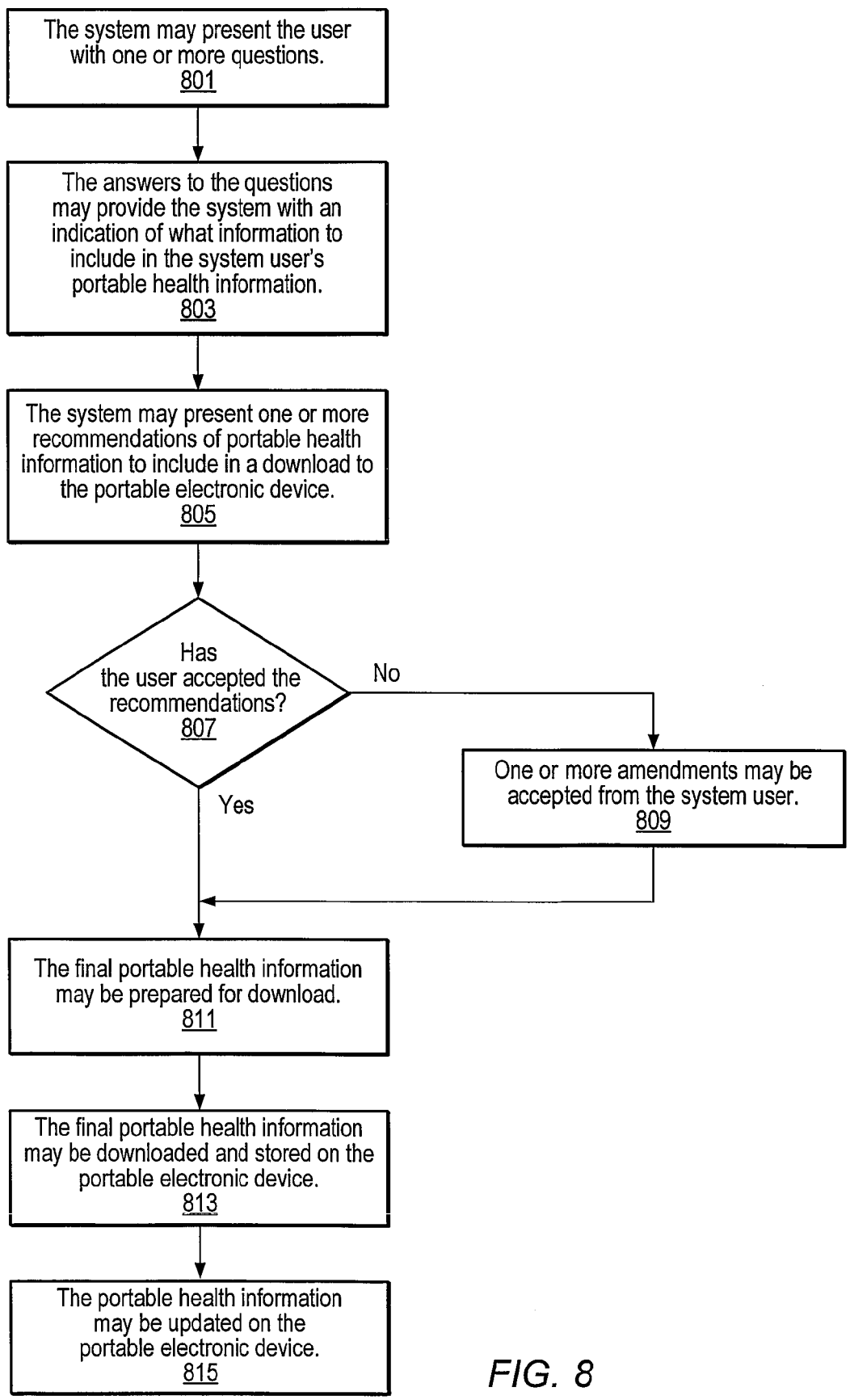
FIG. 8 illustrates a flowchart of a method for a heuristic approach to selecting portable health information for download to the portable electronic device, according to an embodiment.

FIG. 8 illustrates a flowchart of a method for a heuristic approach to selecting portable health information 130 for download to the portable electronic device 140, according to an embodiment. It should be noted that in various embodiments of the methods described below, one or more of the elements described may be performed concurrently, in a different order than shown, or may be omitted entirely. Other additional elements may also be performed as desired.

At 801, the system may present the system user 170 with one or more questions 911 (e.g., see FIG. 9). In some embodiments, the portable medical alert system may present one or more questions 911 to use in determining what information to include in the portable health information 130 to download to the portable electronic device 140. In some embodiments, the system user 170 may be presented with a simple question interface. In some embodiments, an interface 901 may be presented that may include references (e.g., tab 903) to allow the system user 170 to proceed back and forth through the questions 911. For example, tab 905 is highlighted to show the system user 170 what section of the questions 911 the system user 170 is currently in. Subtopics (e.g., subtopic 907) may also be presented to aid navigation through the questions 911. The system user 170 may indicate answers to the questions 911, for example, by clicking (e.g., using an on screen cursor and a computer mouse) "Yes" or "No" interface buttons. Other interface options are also contemplated.

At 803, the answers to the questions 907 may provide the system with an indication of what information to include in the system user's portable health information 130. In some embodiments, questions 907 may be presented heuristically such that the system user's answers may be used by the system to determine the next questions to ask the system user 170. For example, if the system user 170 indicates that the system user 170 wants to include a listing of their current prescriptions, the system may next ask the system user 170 if the current listing is correct or if the system user 170 indicates the system user 170 wants to provide emergency instructions, the next question may ask the system user 170 to provide these instructions. Other questions/links are also contemplated.

Figure 10:
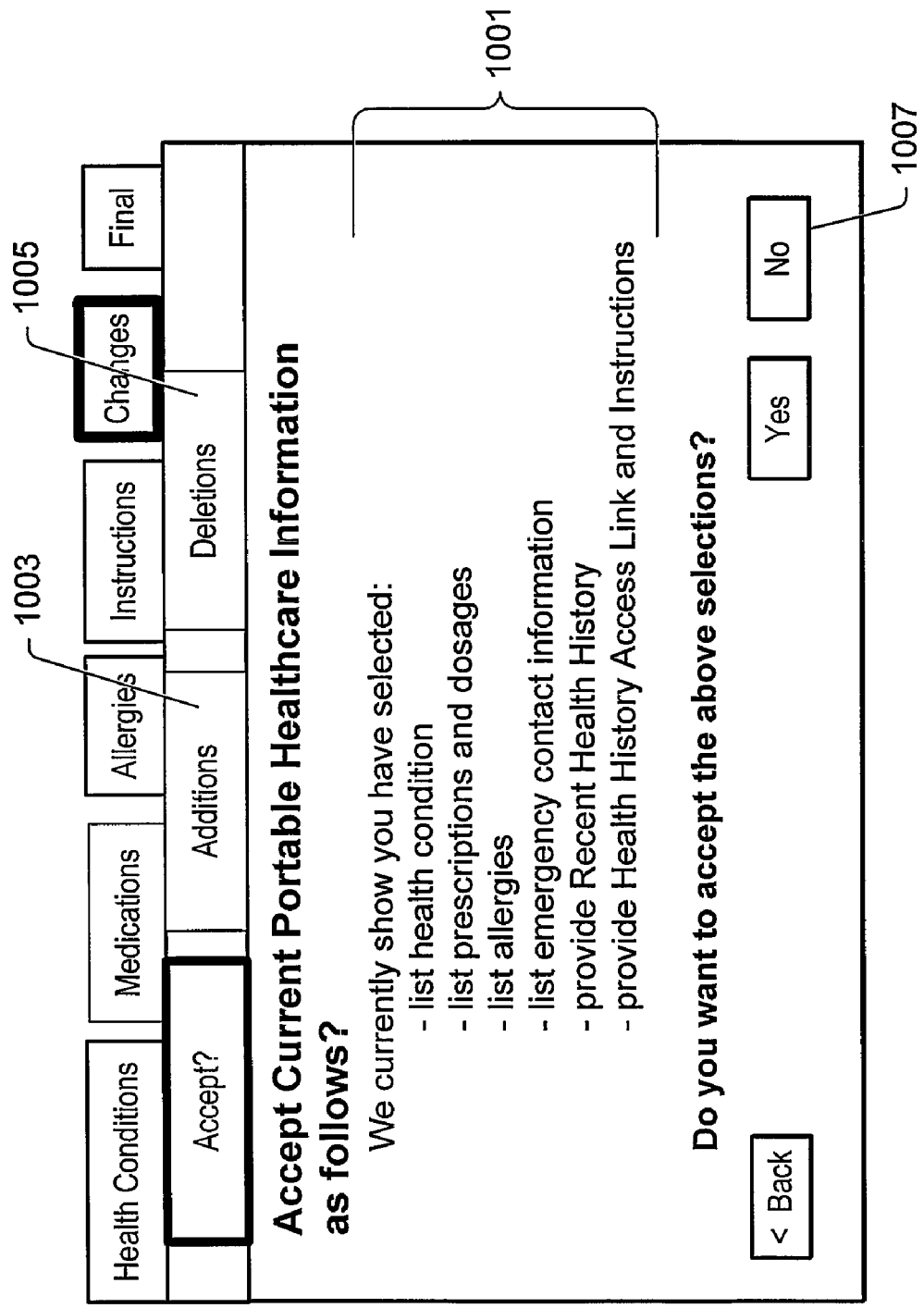
FIG. 10 illustrates a user interface for reviewing system recommendations for the portable health information, according to an embodiment.

At 805, the system may present one or more recommendations of portable health information 130 to include in a download to the portable electronic device 140. The system may determine which information to recommend the system user 170 add to the portable health information 130 based, at least in part, on the system user's input. In some embodiments, the system may determine part (or all) of the portable health information 130 for download (e.g., without user input). For example, the system may determine that, based on the system user's health condition, certain information should be made available to emergency health professionals 190. In some embodiments, the system may present the recommendations (e.g., see recommendations 1001 in FIG. 10) to the system user 170 for approval.

At 807, a determination may be made as to whether the system user 170 has accepted the recommendations 1001. For example, the system user 170 may indicate "Yes" or "No" by clicking the respective button. Other methods for determining whether the system user 170 has accepted the recommendations are also contemplated. For example, the system user 170 may be presented with the list and may press an "Enter" key on their keyboard to accept.

At 809, if the system user 170 has not accepted the recommendations, one or more amendments may be accepted from the system user 170. In some embodiments, the system user 170 may add (e.g., by clicking "No" 1007 or the "Additions" tab 1003) information or delete (e.g., by clicking "No" 1007 or the "Deletions" tab 1005).

At 811, if the system user 170 has accepted the recommendations 1001, and/or sent one or more amendments, the final portable health information 130 may be prepared for download. In some embodiments, the system user 170 may be presented with the final listing 1101 and asked whether to download the portable health information 130. In some embodiments, the download may specify which portable electronic device 140 to download the portable health information 130.

At 813, the portable health information 130 may be downloaded to the portable electronic device 140 (and stored on the portable electronic device 140). The information may be downloaded through a direct physical link (e.g., through a Universal Serial Bus (USB) cable) or wirelessly (e.g., through a Bluetooth™ connection).

At 815, the portable health information may be updated on the portable electronic device 140. In some embodiments, the portable health information may be periodically updated on the portable electronic device 140. In some embodiments, the portable electronic device 140 may check for updates each time it is connected to the system user's computer (or, for example, may check for updates over the Internet). In some embodiments, the updates may be broadcast to the portable electronic device 140 when the updates are available and the portable electronic device 140 is in range of the system user's computer (e.g., and communicating wirelessly). In some embodiments, a system user may perform an initial set-up in which various information filters are defined. Filters may then be used by the system to determine whether future information added to the user's health history should be used to update the portable health information. The system user may not need to interact with the system to update the portable health information, but may instead rely on the filters automatically filtering which information should be used to update the portable health information.

While embodiments of the mobile healthcare alert system are generally described herein in reference to healthcare management application 100, embodiments of the mobile healthcare alert system may be implemented for other types of computer-implemented processes, programs, and applications (which may be collectively identified as computer applications), including financial software programs (e.g., tax preparation programs, payroll programs, etc.). Thus, healthcare management application 100s are used as an example herein, and it is to be understood that the Figures and discussions using healthcare management application 100s as examples are intended to apply to other types of software programs, including financial software programs.

Various components of embodiments of the mobile healthcare alert system as described herein may be executed on one or more computer systems, which may interact with various other devices. One such computer system is illustrated by FIG. 12. In the illustrated embodiment, computer system 1200 includes one or more processors 1210 coupled to a system memory 1220 via an input/output (I/O) interface 1230. The system memory 1220 may include various types of memory devices including hard disks. Computer system 1200 further includes a network interface 1240 coupled to I/O interface 1230, and one or more input/output devices 1250, such as cursor control device 1260, keyboard 1270, audio device 1290, and display(s) 1280. In some embodiments, the system may be coupled to a portable electronic device 140 through an interface 1295 (which may include a physical connection to the portable electronic device 140 or may be wireless). In some embodiments, it is contemplated that embodiments may be implemented using a single instance of computer system 1200, while in other embodiments multiple such systems, or multiple nodes making up computer system 1200, may be configured to host different portions or instances of embodiments. For example, in one embodiment some elements may be implemented via one or more nodes of computer system 1200 that are distinct from those nodes implementing other elements.

In various embodiments, computer system 1200 may be a uniprocessor system including one processor 1210, or a multiprocessor system including several processors 1210 (e.g., two, four, eight, or another suitable number). Processors 1210 may be any suitable processor capable of executing instructions. For example, in various embodiments, processors 1210 may be general-purpose or embedded processors implementing any of a variety of instruction set architectures (ISAs), such as the x86, PowerPC, Scalable Processor Architecture (SPARC), or Million Instructions per Second (MIPS) Instruction Set Architectures (ISAs), or any other suitable ISA. In multiprocessor systems, each of processors 1210 may commonly, but not necessarily, implement the same ISA.

System memory 1220 may be configured to store program instructions and/or data accessible by processor 1210. In various embodiments, system memory 1220 may be implemented using any suitable memory technology, such as static random access memory (SRAM), synchronous dynamic RAM (SDRAM), nonvolatile/Flash-type memory, or any other type of memory. Program instructions and/or data may also be stored, for example, on a hard disk. In the illustrated embodiment, program instructions and data implementing desired functions, such as those described above for the mobile healthcare alert system, are shown stored within system memory 1220 as program instructions 1225 and data storage 1235, respectively. In other embodiments, program instructions and/or data may be received, sent or stored upon different types of computer-accessible media or on similar media separate from system memory 1220 or computer system 1200. Generally speaking, a computer-accessible medium may include storage media or memory media such as magnetic or optical media, e.g., disk or Digital Versatile Disc (DVD) Read Only Memory (ROM)/Compact Disk-Read Only Memory (CD-ROM) coupled to computer system 1200 via I/O interface 1230. Program instructions and data stored via a computer-accessible medium may be transmitted by transmission media or signals such as electrical, electromagnetic, or digital signals, which may be provided via a communication medium such as a network and/or a wireless link, such as may be implemented via network interface 1240.

In one embodiment, I/O interface 1230 may be configured to coordinate I/O traffic between processor 1210, system memory 1220, and any peripheral devices in the device, including network interface 1240 or other peripheral interfaces, such as input/output devices 1250. In some embodiments, I/O interface 1230 may perform any necessary protocol, timing or other data transformations to convert data signals from one component (e.g., system memory 1220) into a format suitable for use by another component (e.g., processor 1210). In some embodiments, I/O interface 1230 may include support for devices attached through various types of peripheral buses, such as a variant of the Peripheral Component Interconnect (PCI) bus standard or the Universal Serial Bus (USB) standard, for example. In some embodiments, the function of I/O interface 1230 may be split into two or more separate components, such as a north bridge and a south bridge, for example. In addition, in some embodiments some or all of the functionality of I/O interface 1230, such as an interface to system memory 1220, may be incorporated directly into processor 1210.

Network interface 1240 may be configured to allow data to be exchanged between computer system 1200 and other devices attached to a network, such as other computer systems, or between nodes of computer system 1200. In various embodiments, network interface 1240 may support communication via wired or wireless general data networks, such as any suitable type of Ethernet network, for example; via telecommunications/telephony networks such as analog voice networks or digital fiber communications networks; via storage area networks such as Fibre Channel Storage Area Networks (SANs), or via any other suitable type of network and/or protocol.

Input/output devices 1250 may, in some embodiments, include one or more display terminals, keyboards, keypads, touchpads, scanning devices, voice or optical recognition devices, or any other devices suitable for entering or retrieving data by one or more computer system 1200. Multiple input/output devices 1250 may be present in computer system 1200 or may be distributed on various nodes of computer system 1200. In some embodiments, similar input/output devices may be separate from computer system 1200 and may interact with one or more nodes of computer system 1200 through a wired or wireless connection, such as over network interface 1240.

As shown in FIG. 12, memory 1220 may include program instructions 1225, configured to implement at least a portion of embodiments of the mobile healthcare alert system as described herein, and data storage 1235, comprising various documents, tables, databases, etc. accessible by program instructions 1225. In one embodiment, program instructions 1225 may include software elements of the mobile healthcare alert system illustrated in the Figures, and data storage 1235 may include data used in embodiments of the mobile healthcare alert system. In other embodiments, different software elements and data may be included. Program instructions and/or data may be stored, for example, on various types of memory including hard disks.

Those skilled in the art will appreciate that computer system 1200 is merely illustrative and is not intended to limit the scope of the mobile healthcare alert system as described herein. In particular, the computer system and devices may include any combination of hardware or software that can perform the indicated functions, including computers, network devices, internet appliances, PDAs 203, mobile phones 201, pagers, etc. Computer system 1200 may also be connected to other devices that are not illustrated, or instead may operate as a stand-alone system. In addition, the functionality provided by the illustrated components may in some embodiments be combined in fewer components or distributed in additional components. Similarly, in some embodiments, the functionality of some of the illustrated components may not be provided and/or other additional functionality may be available.

Those skilled in the art will also appreciate that, while various items are illustrated as being stored in memory or on storage while being used, these items or portions of them may be transferred between memory and other storage devices for purposes of memory management and data integrity. Alternatively, in other embodiments some or all of the software components may execute in memory on another device and communicate with the illustrated computer system via inter-computer communication. Some or all of the system components or data structures may also be stored (e.g., as instructions or structured data) on a computer-accessible medium or a portable article to be read by an appropriate drive, various examples of which are described above. In some embodiments, instructions stored on a computer-accessible medium separate from computer system 700 may be transmitted to computer system 700 via transmission media or signals such as electrical, electromagnetic, or digital signals, provided via a communication medium such as a network and/or a wireless link. Various embodiments may further include receiving, sending or storing instructions and/or data implemented in accordance with the foregoing description upon a computer-accessible medium. Accordingly, the present invention may be practiced with other computer system configurations.

Various embodiments may further include receiving, sending or storing instructions and/or data implemented in accordance with the foregoing description upon a computer-accessible medium. Generally speaking, a computer-accessible medium may include storage media or memory media such as magnetic or optical media, e.g., disk or DVD/CD-ROM, volatile or non-volatile media such as RAM (e.g. Synchronous Dynamic RAM (SDRAM), Double Data Rate RAM (DDR RAM), RAMBUS Dynamic RAM (RDRAM), Static RAM (SRAM), etc.), Read Only Memory (ROM), etc. As well as transmission media or signals such as electrical, electromagnetic, or digital signals, provided via a communication medium such as network and/or a wireless link.

The various methods as illustrated in the Figures and described herein represent exemplary embodiments of methods. The methods may be implemented in software, hardware, or a combination thereof. The order of method may be changed, and various elements may be added, reordered, combined, omitted, modified, etc.

Various modifications and changes may be made as would be obvious to a person skilled in the art having the benefit of this disclosure. It is intended that the invention embrace all such modifications and changes and, accordingly, the above description to be regarded in an illustrative rather than a restrictive sense.

What is claimed is:

1. A system, comprising:
a server device configured to couple to a network, wherein the server device is configured to:
provide one or more heuristic questions to determine what information to include in a system user's health information to be transferred to a portable device, the health information at least including at least one of either psychological information or dental records, and wherein answers to the heuristic questions are used by the system to determine further questions to ask the user, if any;
receiving a recommendation as to one or more recommended portions of the health information to transfer to the portable device, based on the answers to the heuristic questions;
receiving approval from the system user to transfer at least one of the recommended portions of health information to the portable electronic device;
transfer the at least one portion of approved health information to the portable electronic device, wherein the server device is configured to be able to transfer the information to a plurality of portable electronic devices including individual ones of a mobile phone, a personal digital assistant (PDA), a portable audio player, and a portable game player;
automatically transferring health information updates to the portable electronic device at times when the device is coupled to a source for updated health information, the health information contained in any given update being automatically determined using information filters previously setup by the user being applied to new information received at the system user's health information;
wherein the portable electronic device is operable to store the health information, the portable electronic device including a plurality of security tiers, each tier requiring a different type of security identifier for access to health information in that tier, the available types of security identifiers for each tier including a password or PIN provided by the user, a fingerprint of the user, and a retina scan of the user;
wherein the system user provides an indication to a health professional to the existence of the health information stored on the portable electronic device, the health professional being an emergency medical technician, a physician, physician's assistant, a nurse, or an insurance company representative; and
wherein the portable electronic device is operable to provide the health information associated with a given security tier to the health professional upon receiving a security identifier appropriate for the given security tier; and
providing the health information, from an appropriate security tier based on a received security identifier, to the health professional using the portable electronic device.

2. The system as recited in claim 1, wherein the health information includes information about a health condition, a personal health history, personal health record, current medications, current medication dosages, allergies, or instructions.

3. The system as recited in claim 1, wherein the health information comprises a web-based link.

4. The system as recited in claim 1, wherein the health information provided to the portable electronic device is at least partially selected from a collection of health information maintained for the system user on a network based health information system.

5. The system as recited in claim 4, wherein the system user selects the health information through a system user interface provided by the system.

6. The system as recited in claim 4, wherein transferring the health information comprises downloading the health information from a healthcare application.

7. A computer readable storage medium, comprising program instructions, wherein the program instructions are computer-executable to implement:
provide one or more heuristic questions to determine what information to include in a system user's health information to be transferred to a portable device, the health information at least including at least one of either psychological information or dental records, and wherein answers to the heuristic questions are used by the system to determine further questions to ask the user, if any;

receiving a recommendation as to one or more recommended portions of the health information to transfer to the portable device, based on the answers to the heuristic questions;

receiving approval from the system user to transfer at least one of the recommended portions of health information to the portable electronic device;

transfer the at least one portion of approved health information to the portable electronic device, wherein the server device is configured to be able to transfer the information to a plurality of portable electronic devices including individual ones of a mobile phone, a personal digital assistant (PDA), a portable audio player, and a portable game player;

automatically transferring health information updates to the portable electronic device, the health information contained in any given update being automatically determined using information filters previously setup by the user being applied to new information received at the system user's health information;

wherein the portable electronic device is operable to store the health information, the portable electronic device including a plurality of security tiers, each tier requiring a different type of security identifier for access to health information in that tier, the available types of security identifiers for each tier including a password or PIN provided by the user, a fingerprint of the user, and a retina scan of the user;

wherein the system user provides an indication to a health professional to the existence of the health information stored on the portable electronic device, the health professional being an emergency medical technician, a physician, physician's assistant, a nurse, or an insurance company representative; and wherein the portable electronic device is operable to provide the health information associated with a given security tier to the health professional upon receiving a security identifier appropriate for the given security tier; and providing the health information, from an appropriate security tier based on a received security identifier, to the health professional using the portable electronic device.

8. The computer readable storage medium as recited in claim 7, wherein the health information includes information about a health condition, a personal health history, personal health record, current medications, current medication dosages, allergies, or instructions.

9. The computer readable storage medium as recited in claim 7, wherein the health information comprises a web-based link.

10. The computer readable storage medium as recited in claim 7, wherein the user selects the health information through a system user interface provided by a computer system communicatively coupled to the portable electronic device.

11. The computer readable storage medium as recited in claim 7, wherein the health information is downloaded from a healthcare application.

12. The computer readable storage medium as recited in claim 7, wherein the program instructions are further computer executable to automatically transfer updates to the portable electronic device of the previously stored health information stored on the portable electronic device, the information contained in any given update automatically being determined using information filters previously setup by the user.

13. The system of claim 7 wherein the system user's health information is stored on a computing system which periodically communicates with the portable electronic device through wireless means and the updates are broadcast to the wireless portable electronic device when the updates are available.

* * * * *